(12) United States Patent
Brame et al.

(10) Patent No.: US 6,747,273 B2
(45) Date of Patent: Jun. 8, 2004

(54) METHODS OF DETECTING PROTEIN ARGININE METHYLTRANSFERASE, AND USES RELATED THERETO

(75) Inventors: Cynthia J. Brame, Charlottesville, VA (US); Linda McBroom, Toronto (CA)

(73) Assignee: MDS Proteomics Inc., Toronto (CA)

( * ) Notice: Subject to any disclaimer, the term of this patent is extended or adjusted under 35 U.S.C. 154(b) by 0 days.

(21) Appl. No.: 10/152,158

(22) Filed: May 20, 2002

(65) Prior Publication Data

US 2003/0082819 A1 May 1, 2003

Related U.S. Application Data

(60) Provisional application No. 60/292,075, filed on May 18, 2001.

(51) Int. Cl.$^7$ .......................... B01D 59/44; B01D 59/48
(52) U.S. Cl. ....................................... 250/283; 250/282
(58) Field of Search ................................. 250/282, 283

(56) References Cited

PUBLICATIONS

Brostoff et al., "Identification of N–G, N'–G–Dimethylarginine and N–G, N–G–Dimethylarginine in the Basic A1 Protein from Bovine Myelin" (1972) Arch. Biochem. Biophys., 148(1), 156–160.*
Smith et al., "Unusual Sites of Arginine Methylation in Poly(A)–Binding Protein II and in Vitro Methylation by Protein Arginine Methyltransferases PRMT1 and PRMT3" (1999) J. Biol. Chem. 274(19), 13229–13234.*
Brahms et al., "The C–Terminal RG Dipeptide Repeats of the Spliceosome Sm Proteins D1 and D3 Contain Symmetrical Dimethylarginines, Which Form a Major B–Cell Epitope for Anti–Sm Autoantibodies" (2000) J. Biol. Chem., 275(22), 17122–17129.*
Belyanskaya, L.L. et al. Exposure on Cell Surface and Extensive Arginine Methylation of Ewing Sarcoma (EWS) Protein. J. Biol. Chem. 276, 18681–18687 (Jun. 1, 2001).
Brahms, H. et al. Symmetrical Dimethylation of arginine residues in spliceososmal Sm protein B/B' and the Sm–like protein LSm4, and their interaction with the SMN protein. RNA 7, 1531–1542 (2001).

Friesen, W.J. et al. The Methylosome, a 20S Complex Containing JBP1 and plCln, Produces Dimethylarginine–Modified Sm Proteins. Mol. Cell. Biol. 21, 8289–8300 (Dec. 2001).
Friesen, W.J. et al. A Novel WD Repeat Potein Component of the Methylosome Binds Sm Protein. J. Biol. Chem. 277, 8243–8247 (Mar. 8, 2002).
Klein, S. et al. Biochemical Analysis of the Arginine Methylation of High Molecular Weight Fibroblast Growth Factor–2. J. Biol. Chem. 275, 3150–3157 (Feb. 4, 2000).
Meyer, J. et al. High–Performance Liquid Chromatographic Determination of Nitric Oxide Synthase–Related Arginine Derivatives inVitro and in Vivo. Analytical Biochem. 247, 11–16 (1997).
Mowen, K.A. and David, M. Analysis of Protein Arginine Methylation and Protein Argentine–Methyltransferase Activity. Science's stke (Jul. 31, 2001).
Patton, W.F. Detection Technologies in proteome analysis. J. Chromatography B 771, 3–31 (2002).
Pritzker, L.B. et al. Deimination of Myelin Basic Protein. 2. Effect of methylation of MBP on its Deimination by Peptidylarginine Deiminase. Biochem. 39, 5382–5388 (2000).
Rappsilber, J. et al. Detection of arginine dimethylated peptides by precursor ion scanning quadrupole TOF mass spectrometry in positive ion mode. Proc. 49th ASMS Conference on Mass Spectrometry and Allied Topics, Chicago, IL (May 27–31, 2001).

* cited by examiner

*Primary Examiner*—Jon P. Weber
(74) *Attorney, Agent, or Firm*—Ropes & Gray LLP; Matthew P. Vincent

(57) ABSTRACT

This invention relates to methods and reagents for detecting the presence of symmetrically and asymmetrically methylated arginine residues, either along or in polypeptides, using mass spectrometry. It also provides methods of determining structures of methylated arginine residues, methods of identifying substrates of PMRTs, and methods of conducting proteomic business using any of the suitable methods recited above.

7 Claims, 4 Drawing Sheets

Figure 4:
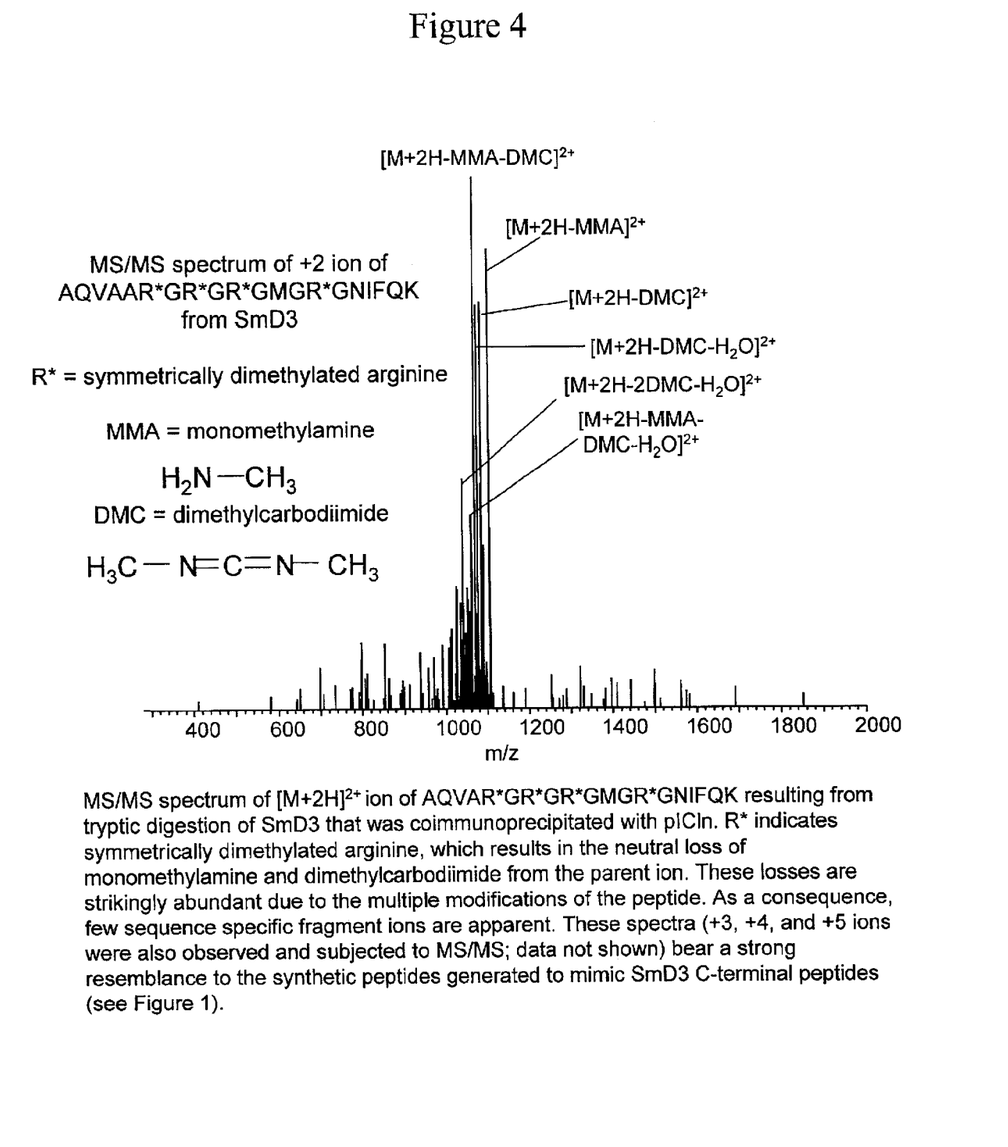
FIG. 4 shows the MS/MS spectrum of peptide AQVAR*GR*GR*GMGR*GNIFQK (SEQ ID NO: 10) resulting from tryptic digestion of SmD3 coimmunoprecipitated with pICln. R* indicates a symmetrically dimethylated arginine residue.

MS/MS spectrum of [M+2H]$^{2+}$ ion of AQVAR*GR*GR*GMGR*GNIFQK resulting from tryptic digestion of SmD3 that was coimmunoprecipitated with pICln. R* indicates symmetrically dimethylated arginine, which results in the neutral loss of monomethylamine and dimethylcarbodiimide from the parent ion. These losses are strikingly abundant due to the multiple modifications of the peptide. As a consequence, few sequence specific fragment ions are apparent. These spectra (+3, +4, and +5 ions were also observed and subjected to MS/MS; data not shown) bear a strong resemblance to the synthetic peptides generated to mimic SmD3 C-terminal peptides (see Figure 1).

SEQUENCE LISTING

```
<160> NUMBER OF SEQ ID NOS: 10

<210> SEQ ID NO 1
<211> LENGTH: 13
<212> TYPE: PRT
<213> ORGANISM: Artificial Sequence
<220> FEATURE:
<223> OTHER INFORMATION: synthetic dimethylated peptide
<220> FEATURE:
<221> NAME/KEY: MISC_FEATURE
<222> LOCATION: (1)..(13)
<223> OTHER INFORMATION: Xaa=methylated Arg

<400> SEQUENCE: 1

Val Ala Gly Xaa Gly Xaa Gly Xaa Gly Gly Pro Arg Arg
1               5                   10

<210> SEQ ID NO 2
<211> LENGTH: 13
<212> TYPE: PRT
<213> ORGANISM: Artificial Sequence
<220> FEATURE:
<223> OTHER INFORMATION: synthetic dimethylated peptide
<220> FEATURE:
<221> NAME/KEY: MISC_FEATURE
<222> LOCATION: (6)..(6)
<223> OTHER INFORMATION: Xaa=methylated Arg

<400> SEQUENCE: 2

Val Ala Gly Arg Gly Xaa Gly Arg Gly Gly Pro Arg Arg
1               5                   10

<210> SEQ ID NO 3
<211> LENGTH: 14
<212> TYPE: PRT
<213> ORGANISM: Artificial Sequence
<220> FEATURE:
<223> OTHER INFORMATION: synthetic dimethylated peptide
<220> FEATURE:
<221> NAME/KEY: MISC_FEATURE
<222> LOCATION: (1)..(14)
<223> OTHER INFORMATION: Xaa=methylated Arg

<400> SEQUENCE: 3

Val Ala Ala Xaa Gly Xaa Gly Xaa Gly Met Gly Xaa Gly Lys
1               5                   10

<210> SEQ ID NO 4
<211> LENGTH: 14
<212> TYPE: PRT
<213> ORGANISM: Artificial Sequence
<220> FEATURE:
<223> OTHER INFORMATION: synthetic dimethylated peptide
<220> FEATURE:
<221> NAME/KEY: MISC_FEATURE
<222> LOCATION: (8)..(8)
<223> OTHER INFORMATION: Xaa=methylated Arg

<400> SEQUENCE: 4

Val Ala Ala Arg Gly Arg Gly Xaa Gly Met Gly Arg Gly Lys
```

-continued

```
1               5                   10
```

```
<210> SEQ ID NO 5
<211> LENGTH: 14
<212> TYPE: PRT
<213> ORGANISM: Artificial Sequence
<220> FEATURE:
<223> OTHER INFORMATION: synthetic dimethylated peptide
<220> FEATURE:
<221> NAME/KEY: MISC_FEATURE
<222> LOCATION: (1)..(14)
<223> OTHER INFORMATION: Xaa=methylated Arg

<400> SEQUENCE: 5

Val Gly Gly Xaa Gly Xaa Gly Xaa Gly Thr Ala Ala Pro Arg
1               5                   10

<210> SEQ ID NO 6
<211> LENGTH: 8
<212> TYPE: PRT
<213> ORGANISM: Artificial Sequence
<220> FEATURE:
<223> OTHER INFORMATION: synthetic dimethylated peptide
<220> FEATURE:
<221> NAME/KEY: MISC_FEATURE
<222> LOCATION: (1)..(8)
<223> OTHER INFORMATION: Xaa=methylated Arg

<400> SEQUENCE: 6

Leu Gly Gly Xaa Gly Xaa Gly Arg
1               5

<210> SEQ ID NO 7
<211> LENGTH: 11
<212> TYPE: PRT
<213> ORGANISM: Artificial Sequence
<220> FEATURE:
<223> OTHER INFORMATION: synthetic dimethylated peptide
<220> FEATURE:
<221> NAME/KEY: MISC_FEATURE
<222> LOCATION: (1)..(11)
<223> OTHER INFORMATION: Xaa=methylated Arg

<400> SEQUENCE: 7

Asn Ser Ser Xaa Ser Xaa Phe Tyr Ser Gly Phe
1               5                   10

<210> SEQ ID NO 8
<211> LENGTH: 8
<212> TYPE: PRT
<213> ORGANISM: Artificial Sequence
<220> FEATURE:
<223> OTHER INFORMATION: synthetic dimethylated peptide
<220> FEATURE:
<221> NAME/KEY: MISC_FEATURE
<222> LOCATION: (2)..(2)
<223> OTHER INFORMATION: Xaa=methylated Arg

<400> SEQUENCE: 8

Gly Xaa Gly Leu Ser Leu Ser Arg
1               5

<210> SEQ ID NO 9
<211> LENGTH: 12
<212> TYPE: PRT
<213> ORGANISM: Artificial Sequence
<220> FEATURE:
<223> OTHER INFORMATION: synthetic dimethylated peptide
<220> FEATURE:
<221> NAME/KEY: MISC_FEATURE
```

```
<222> LOCATION: (6)..(6)
<223> OTHER INFORMATION: Xaa=methylated Arg

<400> SEQUENCE: 9

Arg Pro Ile Gly Gly Xaa Gly Gly Tyr Tyr Gly Ala
1               5                   10

<210> SEQ ID NO 10
<211> LENGTH: 19
<212> TYPE: PRT
<213> ORGANISM: Artificial Sequence
<220> FEATURE:
<223> OTHER INFORMATION: synthetic dimethylated peptide
<220> FEATURE:
<221> NAME/KEY: MISC_FEATURE
<222> LOCATION: (1)..(19)
<223> OTHER INFORMATION: Xaa=methylated Arg

<400> SEQUENCE: 10

Ala Gln Val Ala Xaa Gly Xaa Gly Xaa Gly Met Gly Xaa Gly Asn Ile
1               5                   10                  15

Phe Gln Lys
```

METHODS OF DETECTING PROTEIN ARGININE METHYLTRANSFERASE, AND USES RELATED THERETO

REFERENCE TO RELATED APPLICATION

This Application claims priority to U.S. Provisional Application No. 60/292,075, filed on May 18, 2001, the entire content of which is hereby incorporated by reference.

BACKGROUND OF THE INVENTION

Post-translational modifications can have profound effects on the activities of proteins. One type of protein modification involves the transfer of methyl groups to a specific arginine residue resulting in the formation of dimethylarginine. This reaction is catalyzed by a protein arginine methyltransferase (PRMT). PRMTs have been implicated in a variety of processes, including cell proliferation, signal transduction, and protein trafficking. Arginine dimethylation has been implicated in such cellular processes as transcription (Chen et al. 1999 Science 284:2174–7), signal transduction (Bedford et al. 2000 J Biol Chem 275:16030–6; Mowen et al. 2001 Cell 104:731–41), nuclear export (Shen et al. 1998 Genes Dev. 12:679–91), myelin integrity (Kim et al. 1997 Int J Biochem Cell Biol 29:743–51) and possibly antigenicity (Brahms et al. 2000 J Biol Chem 275:17122–9).

Figure 1:
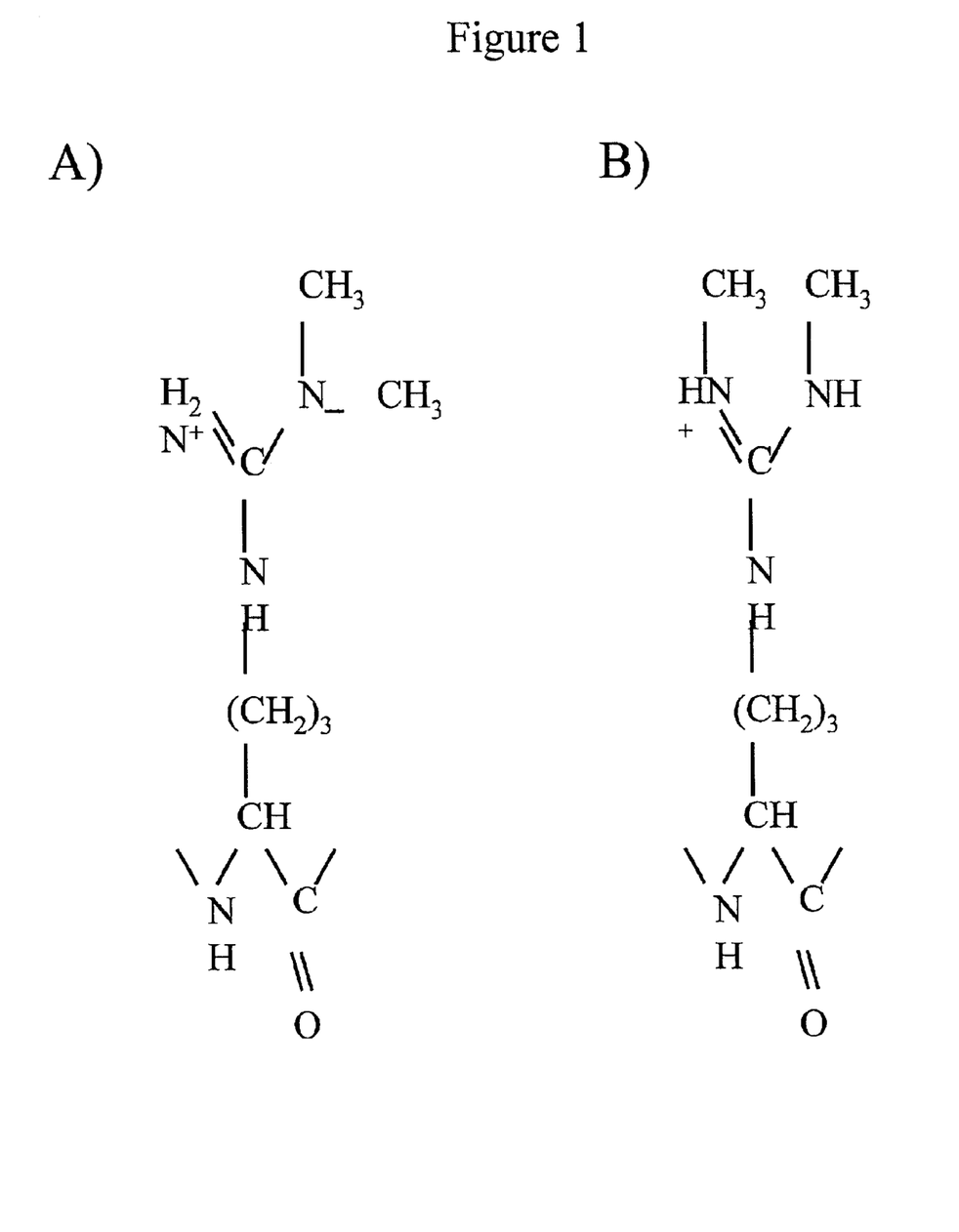
FIG. 1 illustrates that there are two classes of dimethylarginine species that can be produced by PRMTs. Type I PRMTs produce asymmetric $N^G$, $N^G$ dimethylarginine residues, while type II PRMTs produce symmetric $N^G$, $N^{'G}$ dimethylarginines.

Methylation of arginine residues is one of many covalent modifications of eukaryotic proteins that occur concomitant with or shortly following translation. There are two classes of PRMTs that differ in the type of dimethylarginine that they produce. Type I PRMTs produce asymmetric $N^G$, $N^G$ dimethylarginine residues, while type II PRMTs produce symmetric $N^G$, $N^{'G}$ dimethylarginines (FIG. 1). See also Gary et al. 1998 Prog. Nucleic Acid Res. 61:65–133).

Most substrates for type I enzymes bind nucleic acid, usually RNA. These include heterogeneous nuclear RNA binding proteins (hnRNPs), which collectively contain 65% of the nuclear asymmetric dimethylarginine, as well as fibrillarin and nucleolin (Lischwe et al. 1985 J. Biol. Chem. 260:14304–14310; Liu et al. 1995 Mol. Cell. Biol. 15:2800–2808; Najbauer et al. 1993 J. Biol. Chem. 268:10501–10509). Examples of physiological substrate of symmetric (type II) arginine methyltransferase include myelin basic protein, a major protein component of the myelin sheath, as well as the Sm proteins D1 and D3, which are components of small nuclear ribonucleoproteins.

Genes encoding rat (PRMT1), human (HRMT1L2), and yeast (RMT1) type I enzymes have been characterized (Gary et al. 1996 J. Biol. Chem. 271:12585–12594; Henry et al. 1996 Mol. Cell. Biol. 16:3668–3678; Lin et al. 1996 J. Biol. Chem. 271:15034–15044; Scott et al. 1998 Genomics 48:330–340). The mammalian genes appear to be ubiquitously expressed in all tissues (Lin et al. supra; Scott et al. supra; Tang et al. 1998 J. Biol. Chem. 273:16935–16945).

Type I enzymes have been implicated in a variety of processes, including cell growth control, signal transduction, and protein trafficking. The enzymes preferentially methylate motifs rich in arginine and glycine (RGG boxes), a common feature of the RNA binding domains of hnRNPs (Liu et al. 1995 Mol. Cell. Biol. 15:2800–2808). Arginine-methylated hnRNP A1, but not Hrp1p, has lower affinity for RNA than the native protein, suggesting a potential mechanism for modulation of protein-RNA interactions. Levels of protein methylarginine may change in response to extracellular stimuli under circumstances in which biological responses are also suppressed by methyltransferase inhibitors. These include nerve growth factor-induced neurite outgrowth in PC12 cells and mitogenic responses of lipopolysaccharide-treated B cells.

Interactions between the PRMT1 enzyme and potential signaling components have also emerged from yeast two-hybrid screens. The immediate-early gene product TIS21 (BTG2) and the leukemia-associated gene product BTG1 interact with PRMT1 and can modulate its enzymatic activity in vitro. TIS21 and BTG1 both belong to a family of mitogen-induced proteins implicated in negative regulation of the cell cycle. PRMT1 also binds to the cytoplasmic domain of the IFNAR1 chain of the alpha beta interferon receptor, while growth-inhibitory effects of interferon were suppressed by antisense oligonucleotides directed against the methyltransferase. Finally, a novel arginine methyltransferase (CARM1) associates with p160 coactivators and serves as a secondary coactivator of nuclear hormone receptors.

Other studies have identified a role for arginine methylation in protein trafficking. Shuttling of the yeast hmRNP-related proteins Np13p and Hrp1p between the nucleus and cytoplasm requires methylation by the Hmt1p methyltransferase. The human enzyme complements the shuttling defect, suggesting functional conservation between the two enzymes. Nuclear translocation of the large form of basic fibroblast growth factor may also depend on arginine methylation. In the presence of a methyltransferase inhibitor, basic fibroblast growth factor was not methylated and the protein did not localize to the nucleus.

The prevalence of $N^G,N^G$-dimethylarginine in RNA binding proteins and conservation among protein arginine N-methyltransferases underscore the potential biological importance of this posttranslational modification. However, a major issue arguing against a dynamic role for the type I enzymes in cell regulation concerns the possibility that arginine methylation is both constitutive and irreversible. While most substrates have not been characterized, some are known to exist only in a fully methylated state. Moreover, no demethylase capable of removing dimethylarginine residues has been identified and in the case of histones, turnover of dimethylarginine accompanies protein degradation.

Efforts to understand the biochemical function of mammalian arginine methyltransferases are complicated by several factors, including the existence of multiple enzymes and the fact that methyltransferase inhibitors nonspecifically target multiple processes in which S-adenosylmethionine serves as a methyl donor. In yeast, functional studies of arginine methylation have benefited greatly from genetic approaches that have led to the isolation of cells deficient in the enzyme. In principle, gene targeting strategies could be used for similar studies of the mammalian enzymes, assuming that the proteins are not required for cell viability.

It is likely that the different classes of PRMTs will regulate different cellular targets and pathways as the known substrates for class I and class II PRMTs appear to be distinct from each other. It is an object of the present invention to provide methods and systems that can detect methylarginine residues in polypeptide samples, and can differentiate between symmetric and asymmetric dimethylation.

SUMMARY OF THE INVENTION

One aspect of the present invention provides a method for identifying the structure of a dimethylarginine, e.g., to distinguish between symmetrical and asymmetrical dimethylarginine residues. In certain embodiments, the subject method includes obtaining, by mass spectroscopy, a neutral loss spectra of a peptide containing a dimethylarginine. From the neutral loss spectra, the neutral loss, if any, of monomethylamine, dimethylcarbodiimide, and/or the neutral loss of dimethylamine is determined. Neutral loss of monomethylamine and dimethylcarbodiimide indicates the presence of a symmetrically dimethylated arginine residue. On the other hand, neutral loss of dimethylamine indicates the presence of a asymmetrically dimethylated arginine residue.

Another aspect of the present invention provides a method for identifying dimethylarginine residues in a test peptide. In general, the method includes identifying the presence of dimethylarginine residues from mass spectra of a sample peptide obtained under conditions in which the spectra reveal mass modification by methylation, if any, of arginine residue in the sample peptide. For dimethylarginine residue which are identified, the method also ascertains the nature of the methylation by determining if a neutral loss spectra of the sample peptide shows one or both of neutral loss of monomethylamine, dimethylcarbodiimide, and/or neutral loss of dimethylamine. Neutral loss of monomethylamine and of dimethylcarbodiimide indicates the presence of a symmetrically dimethylated arginine residue whereas neutral loss of dimethylamine indicates the presence of a asymmetrically dimethylated arginine residue.

Still another aspect of the invention provides a method for identifying substrates of a protein arginine methyltransferase. According to the subject embodiment, mass spectra are obtained for one or more sample polypeptides which have been exposed to a protein arginine methyltransferase (PRMT) under conditions wherein methylation, if any, of arginine residues in a substrate protein of the PRMT can occur. The presence of dimethylarginine residues in the sample polypeptide can be identified by the presence of mass modified arginine (relative to unmodified arginine) in the mass spectra of the sample protein. To ascertain the nature of the methylation of a dimethylarginine residue, further determines if a neutral loss spectra of the sample peptide shows one or both of neutral loss of monomethylamine, dimethylcarbodiimide, and/or neutral loss of dimethylamine. Neutral loss of monomethylamine and of dimethylcarbodiimide indicates the presence of a symmetrically dimethylated arginine residue whereas neutral loss of dimethylamine indicates the presence of a asymmetrically dimethylated arginine residue. In certain preferred embodiments, the sequence of at least that portion of a polypeptide including a dimethylarginine residue is determined, e.g., based on the mass spectra of the polypeptide. The subject method can be carried out for a library of sample polypeptides.

Thus, the invention provides A method for identifying substrates of a protein arginine methyltransferase comprising: (i) obtaining mass spectra for one or more sample polypeptides which have been exposed to a protein arginine methyltransferase (PRMT) under conditions wherein methylation, if any, of arginine residues in a substrate protein of the PRMT can occur; (ii) identifying the presence of dimethylarginine residues in the sample polypeptide by the presence of mass modified arginine in the mass spectra; and (iii) ascertaining the nature of the methylation of a dimethylarginine residue identifying in step (i) by determining if a neutral loss spectra of the sample peptide shows one or both of neutral loss of monomethylamine (MMA), dimethylcarbodiimide (DMC), and/or neutral loss of dimethylamine (DMA), wherein neutral loss of monomethylamine (MMA) and of dimethylcarbodiimide (DMC) indicates the presence of a symmetrically dimethylated arginine residue whereas neutral loss of dimethylamine (DMA) indicates the presence of a asymmetrically dimethylated arginine residue.

In certain embodiments, the method further comprising determining the substrate specificity of a protein arginine methyltransferase by determining the sequence of at least that portion of a polypeptide including a dimethylarginine residue.

In certain embodiments, said one or more sample polypeptides constitute a library of sample polypeptides.

In certain embodiments of the above methods, the neutral loss spectra is generated from the mass spectra.

In certain embodiments of the above methods, the spectra are obtained using a mass spectrometer in which ionization of the sample protein is accomplished matrix-assisted laser desorption (MALDI) ionization, electrospray (ESI), or electron impact (EI). In certain preferred embodiments, the spectra are obtained using ESI-MS/MS.

Another aspect of the invention provides mass spectrometry system including an automated system for identifying dimethylarginine residues in a test peptide, which automated system comprises: (i) a methylation detection system that (a) analyzes one or more mass spectra obtained under conditions in which the spectra reveal mass modification by methylation, if any, of arginine residue in a sample peptide, and (b) identifies the presence of dimethylarginine residues from characteristic mass differences between arginine and dimethylarginine in the mass spectra; (ii) a neutral loss detection system for determining the nature of the methylation of a dimethylarginine residue identified by the methylation detection system, which neutral loss detection system determines if a neutral loss spectra of the sample peptide shows one or both of neutral loss of monomethylamine (MMA), dimethylcarbodiimide (DMC), and/or neutral loss of dimethylamine (DMA), wherein neutral loss of monomethylamine (MMA) and of dimethylcarbodiimide (DMC) indicates the presence of a symmetrically dimethylated arginine residue, whereas neutral loss of dimethylamine (DMA) indicates the presence of a asymmetrically dimethylated arginine residue.

Another aspect of the invention provides a method of conducting a drug discovery business. The method utilizes any of the above methods to determine the identity of a PRMT and substrate thereof. Agents are identified by their ability to alter the level of methylation of the substrate. Therapeutic profiling of identified agents, or further analogs thereof, for efficacy and toxicity in animals are accomplished, and pharmaceutical preparations are formulated including one or more agents identified as having an acceptable therapeutic profile. The subject method can include an additional step of establishing a distribution system for distributing the pharmaceutical preparation for sale, and may optionally include establishing a sales group for marketing the pharmaceutical preparation.

Thus the invention provides A method of conducting a drug discovery business, comprising: (i) by the method of any of claims 1–8, determining the identity of a PRMT and substrate thereof; (ii) identifying agents by their ability to alter the level of methylation of the substrate; (iii) conducting therapeutic profiling of agents identified in step (ii), or further analogs thereof, for efficacy and toxicity in animals; and (iv) formulating a pharmaceutical preparation including one or more agents identified in step (iii) as having an acceptable therapeutic profile.

In one embodiment, the method further includes an additional step of establishing a distribution system for distributing the pharmaceutical preparation for sale, and may optionally include establishing a sales group for marketing the pharmaceutical preparation.

Yet another aspect of the present invention provides a method of conducting a proteomics business. The method utilizes any of the above methods to determine the identity of a PRMT and substrate thereof. Rights for further drug development of agents that alter the level of methylation of the substrate are licensed to a third party.

Another aspect of the present invention relates to a protein sequence or coding sequence database comprising annotation information representative of the methylation status (see below) of arginine residues or arginine-containing polypeptides.

Still another aspect of the present invention provides a mass spectrometry system including an automated system for identifying dimethylarginine residues in a test peptide. The automated system generally includes: (i) a methylation detection system that (a) analyzes one or more mass spectra obtained under conditions in which the spectra reveal mass modification by methylation, if any, of arginine residue in a sample peptide, and (b) identifies the presence of dimethylarginine residues from characteristic mass differences between arginine and dimethylarginine in the mass spectra; (ii) a neutral loss detection system for determining the nature of the methylation of a dimethylarginine residue identified by the methylation detection system, which neutral loss detection system determines if a neutral loss spectra of the sample peptide shows one or both of neutral loss of monomethylamine, dimethylcarbodiimide, and/or neutral loss of dimethylamine.

In one embodiment, the methylation detection system comprises a commercially available mass spectrometer possessing the ability to detect post translational modification, such as methylation. In another embodiment, the neutral loss detection system is part of a commercial mass spectrometer (such as a Thermo Finnigan mass spectrometer).

In preferred embodiments, the methylation detection and neutral loss detection systems are software components running on a computer which acquires mass spectra from a spectrometer.

DETAILED DESCRIPTION OF THE INVENTION

I. Overview

The present invention relates to the development of a mass spectrometry-based assay for protein arginine methyltransferases which can be used to differentiate between asymmetric and symmetric dimethylarginines in a protein substrate, and therefore between class I and class II PRMTs. The appended examples demonstrate in further detail that, for example, fragmentation of a peptide containing either symmetric dimethylarginine or asymmetric dimethylarginine produces characteristic neutral losses that can be used to identify which type of dimethylarginine is present in a peptide sample.

Previously published reports have used Mass Spectroscopy to identify the presence of dimethylarginine within a specific peptide of interest, based on the mass of the modified arginine residue (Brahms et al. 2000 *J Biol Chem* 275(22):17122; Belyanskaya et al. (2001) *J Biol Chem* Mar. 9, 2001 [epub ahead of print] manuscript M011446200 PMID: 11278906). In each of these reports a second method has been require to determine which type of dimethylarginine (symmetric or asymmetric) is present.

In contrast, the subject method can be carried out by observing the loss of a characteristic neutral species during, for example, MS/MS fragmentation of peptides. That is, methods according to the invention can be used to generate neutral loss spectra—a spectrum of a plurality of parent ions which produce daughter ions by the loss of the same characteristic neutral fragment. An advantage to the subject method is that it permits the simultaneous identification of peptides containing dimethylarginines and the determination of the type of dimethylarginine present. The present method also offers the advantage of being able to rapidly screen large numbers of peptides for the characteristic neutral losses, thereby determining which ones contain dimethylarginines and are therefore potential substrates for PRMTs.

In certain embodiments, the subject assay can be used to identify an unknown protein substrate for PRMTs, by identifying and sequencing dimethylarginine-containing proteins of interest. In many cases this technique may be used to identify the exact arginine residue that is modified within the protein.

In certain embodiments, the subject method utilizes a mass spectrometer in which ionization of the sample protein is accomplished matrix-assisted laser desorption (MALDI) ionization, electrospray (ESI), or electron impact (EI). For instance, the subject method can be accomplished using a mass spectrometer which is of the ESI-MS/MS type. In other embodiments, the spectrometer is a MALDI-TOF.

In accordance with the present method, modified amino acid identification is performed using mass spectrometers and conditions of analysis permitting fragments, i.e., fragment ions, having the same nominal mass but different exact masses to be resolved. With the present method, exact masses can be resolved at levels at least as low as about 400 ppm, and desirably lower than about 250 ppm. Mass values of 50 milliDaltons (mDa) can be differentiated by the present method. Such sensitivity can be achieved using a variety of different mass spectrometers. In certain preferred embodiments, these will include particularly the hybrid instruments that operate in the tandem MS/MS mode.

To illustrate, a peptide sample can be obtained by treating a crude peptide sample derived from enzymatic digests of proteins, for instance obtained by immunoprecipitation with antibody to a modified amino acid of interest, to enrich for those proteins containing the modified amino acid. In a specific embodiment, the peptide sample is obtained by enzymaticly cleaving proteins after immunoprecipitation of a crude protein sample using phosphotyrosine affinity agents, such as antibodies, thereby to enrich for peptides incorporating phosphotyrosine residues.

In tandem MS/MS instruments, the peptide sample, usually in the form of a tryptic or tryptic-like (with the most C-terminal residue being Arg or Lys) protein digest, is typically injected as an ionized electrospray into a first mass analyzer to yield a first mass spectrum of the ions present in the mixture ("normal" mass spectrum). Each ion can then be channeled selectively (i.e., the precursor or parent ion), into a fragmentation chamber in which fragment ions are generated from each precursor ion. The fragment ions are then moved into a second mass analyzer, to yield a mass spectrum for the fragment ions. From the mass spectra generated in the first mass analyzer, for the precursor ions, it is possible by deduction from both mass spectral databases and protein sequence databases, to identify many known proteins.

Moreover, there are a variety of computer systems which can be readily adapted for automating the identification of neutral losses in the spectra of the present method. For instance, the program "Neutral Loss Tool" has previously been developed to screen MS/MS spectra for user-defined neutral losses (Zarling et al. 2000 *J. Exp. Med.* 192:1755–1762). This method of screening has been successful in culling phosphopeptide MS/MS spectra from data-dependent LC/MS analyses and can be applied to detection of peptides containing dimethyl-arginine as well.

Filtering for MS/MS spectra that contain these diagnostic ions will rapidly pinpoint a potential methyltransferase substrates; the sequence of the peptides, and thus the protein from which they arise, can then be discerned from other fragmentation information within the spectrum. This method of screening therefore may prove quite valuable in determining novel methyltransferase substrates.

II. Definitions

For convenience, certain terms employed in the specification, examples, and appended claims are collected here.

The term "agent" refers broadly to molecules such as proteins, peptides, nucleic acids, carbohydrates, small organic molecules, or natural product extract libraries, such as isolated from animals, plants, fungus and/or microbes. When referring to a nucleic acid, it means a nucleic acid which, itself, its transcriptional product and/or translation product thereof have some biological activity in a cell. Thus, in that case, the term includes coding sequences for polypeptides, antisense constructs, decoy constructs, etc.

As used herein, "methylation status" includes information such as whether a specific amino acid or a polypeptide is methylated. It also includes information such as whether a methylated residue is symmetrically or asymmetrically methylated. The specific amino acid is preferably arginine. The methylation is preferably carried out by Protein Arginine Methyl-Transferase (PRMT), including types I and II PRMTs. When referring to the methylation status of a polypeptide that may contain more than one arginine residues, methylation status may also include information such as the position of each arginine residues on the polypeptide, and the methylation status of each arginine residues on the polypeptide. Additionally, methylation status may also include information such as percentage (or ranges of percentages) of a given residue that is methylated vs. unmethylated under a specific or typical condition, and/or percentage (or ranges of percentages) that a given residue is symmetrically vs. asymmetrically methylated in a population. It should be understood that the methylation status of a given amino acid or polypeptide may vary depending on a number of conditions, including but are not limited to: the specific PRMT used for the methylation reaction, the specific reaction condition, the polypeptide sequence content (longer vs. shorter fragments) surrounding the residue that can be methylated, etc.

"Neutral loss spectra" is a spectrum of a plurality of parent ions which produce daughter ions by the loss of the same characteristic neutral fragment. Neutral loss spectra may be generated from mass spectra data, sometimes with the aid of a computer software.

III. Mass Spectrometers and Detection Methods

Mass Spectrometry

Mass spectrometry, also called mass spectroscopy, is an instrumental approach that allows for the gas phase generation of ions as well as their separation and detection. The five basic parts of any mass spectrometer include: a vacuum system; a sample introduction device; an ionization source; a mass analyzer; and an ion detector. A mass spectrometer determines the molecular weight of chemical compounds by ionizing, separating, and measuring molecular ions according to their mass-to-charge ratio (m/z). The ions are generated in the ionization source by inducing either the loss or the gain of a charge (e.g. electron ejection, protonation, or deprotonation). Once the ions are formed in the gas phase they can be electrostatically directed into a mass analyzer, separated according to mass and finally detected. The result of ionization, ion separation, and detection is a mass spectrum that can provide molecular weight or even structural information.

A common requirement of all mass spectrometers is a vacuum. A vacuum is necessary to permit ions to reach the detector without colliding with other gaseous molecules. Such collisions would reduce the resolution and sensitivity of the instrument by increasing the kinetic energy distribution of the ion's inducing fragmentation, or preventing the ions from reaching the detector. In general, maintaining a high vacuum is crucial to obtaining high quality spectra.

The sample inlet is the interface between the sample and the mass spectrometer. One approach to introducing sample is by placing a sample on a probe which is then inserted, usually through a vacuum lock, into the ionization region of the mass spectrometer. The sample can then be heated to facilitate thermal desorption or undergo any number of high-energy desorption processes used to achieve vaporization and ionization.

Capillary infusion is often used in sample introduction because it can efficiently introduce small quantities of a sample into a mass spectrometer without destroying the vacuum. Capillary columns are routinely used to interface the ionization source of a mass spectrometer with other separation techniques including gas chromatography (GC) and liquid chromatography (LC). Gas chromatography and liquid chromatography can serve to separate a solution into its different components prior to mass analysis. Prior to the 1980's, interfacing liquid chromatography with the available ionization techniques was unsuitable because of the low sample concentrations and relatively high flow rates of liquid chromatography. However, new ionization techniques such as electrospray were developed that now allow LC/MS to be routinely performed. One variation of the technique is that high performance liquid chromatography (HPLC) can now be directly coupled to mass spectrometer for integrated sample separation/preparation and mass spectrometer analysis.

In terms of sample ionization, two of the most recent techniques developed in the mid 1980's have had a significant impact on the capabilities of Mass Spectrometry: Electrospray Ionization (ESI) and Matrix Assisted Laser Desorption/Ionization (MALDI). ESI is the production of highly charged droplets which are treated with dry gas or heat to facilitate evaporation leaving the ions in the gas phase. MALDI uses a laser to desorb sample molecules from a solid or liquid matrix containing a highly UV-absorbing substance.

The MALDI-MS technique is based on the discovery in the late 1980s that an analyte consisting of, for example, large nonvolatile molecules such as proteins, embedded in a solid or crystalline "matrix" of laser light-absorbing molecules can be desorbed by laser irradiation and ionized from the solid phase into the gaseous or vapor phase, and accelerated as intact molecular ions towards a detector of a mass spectrometer. The "matrix" is typically a small organic acid mixed in solution with the analyte in a 10,000:1 molar ratio of matrix/analyte. The matrix solution can be adjusted to neutral pH before mixing with the analyte.

The MALDI ionization surface may be composed of an inert material or else modified to actively capture an analyte. For example, an analyte binding partner may be bound to the surface to selectively absorb a target analyte or the surface may be coated with a thin nitrocellulose film for nonselective binding to the analyte. The surface may also be used as a reaction zone upon which the analyte is chemically modified, e.g., CNBr degradation of protein. See Bai et al, Anal. Chem. 67, 1705–1710 (1995).

Metals such as gold, copper and stainless steel are typically used to form MALDI ionization surfaces. However, other commercially-available inert materials (e.g., glass, silica, nylon and other synthetic polymers, agarose and other carbohydrate polymers, and plastics) can be used where it is desired to use the surface as a capture region or reaction zone. The use of Nation and nitrocellulose-coated MALDI probes for on-probe purification of PCR-amplified gene sequences is described by Liu et al., Rapid Commun. Mass Spec. 9:735–743 (1995). Tang et al. have reported the attachment of purified oligonucleotides to beads, the tethering of beads to a probe element, and the use of this technique to capture a complimentary DNA sequence for analysis by MALDI-TOF MS (reported by K. Tang et al., at the May 1995 TOF-MS workshop, R. J. Cotter (Chairperson); K. Tang et al., Nucleic Acids Res. 23, 3126–3131, 1995). Alternatively, the MALDI surface may be electrically- or magnetically activated to capture charged analytes and analytes anchored to magnetic beads respectively.

Aside from MALDI, Electrospray Ionization Mass Spectrometry (ESI/MS) has been recognized as a significant tool used in the study of proteins, protein complexes and biomolecules in general. ESI is a method of sample introduction for mass spectrometric analysis whereby ions are formed at atmospheric pressure and then introduced into a mass spectrometer using a special interface. Large organic molecules, of molecular weight over 10,000 Daltons, may be analyzed in a quadrupole mass spectrometer using ESI.

In ESI, a sample solution containing molecules of interest and a solvent is pumped into an electrospray chamber through a fine needle. An electrical potential of several kilovolts may be applied to the needle for generating a fine spray of charged droplets. The droplets may be sprayed at atmospheric pressure into a chamber containing a heated gas to vaporize the solvent. Alternatively, the needle may extend into an evacuated chamber, and the sprayed droplets are then heated in the evacuated chamber. The fine spray of highly charged droplets releases molecular ions as the droplets vaporize at atmospheric pressure. In either case, ions are focused into a beam, which is accelerated by an electric field, and then analyzed in a mass spectrometer.

Because electrospray ionization occurs directly from solution at atmospheric pressure, the ions formed in this process tend to be strongly solvated. To carry out meaningful mass measurements, solvent molecules attached to the ions should be efficiently removed, that is, the molecules of interest should be "desolvated." Desolvation can, for example, be achieved by interacting the droplets and solvated ions with a strong countercurrent flow (6–9 l/m) of a heated gas before the ions enter into the vacuum of the mass analyzer.

Other well-known ionization methods may also be used. For example, electron ionization (also known as electron bombardment and electron impact), atmospheric pressure chemical ionization (APCI), fast atom Bombardment (FAB), or chemical ionization (CI).

Immediately following ionization, gas phase ions enter a region of the mass spectrometer known as the mass analyzer. The mass analyzer is used to separate ions within a selected range of mass to charge ratios. This is an important part of the instrument because it plays a large role in the instrument's accuracy and mass range. Ions are typically separated by magnetic fields, electric fields, and/or measurement of the time an ion takes to travel a fixed distance.

If all ions with the same charge enter a magnetic field with identical kinetic energies a definite velocity will be associated with each mass and the radius will depend on the mass. Thus a magnetic field can be used to separate a monoenergetic ion beam into its various mass components. Magnetic fields will also cause ions to form fragment ions. If there is no kinetic energy of separation of the fragments the two fragments will continue along the direction of motion with unchanged velocity. Generally, some kinetic energy is lost during the fragmentation process creating noninteger mass peak signals which can be easily identified. Thus, the action of the magnetic field on fragmented ions can be used to give information on the individual fragmentation processes taking place in the mass spectrometer.

Electrostatic fields exert radial forces on ions attracting them towards a common center. The radius of an ion's trajectory will be proportional to the ion's kinetic energy as it travels through the electrostatic field. Thus an electric field can be used to separate ions by selecting for ions that travel within a specific range of radii which is based on the kinetic energy and is also proportion to the mass of each ion.

Quadrupole mass analyzers have been used in conjunction with electron ionization sources since the 1950s. Quadrupoles are four precisely parallel rods with a direct current (DC) voltage and a superimposed radio-frequency (RF) potential. The field on the quadrupoles determines which ions are allowed to reach the detector. The quadrupoles thus function as a mass filter. As the field is imposed, ions moving into this field region will oscillate depending on their mass-to-charge ratio and, depending on the radio frequency field, only ions of a particular m/z can pass through the filter. The m/z of an ion is therefore determined by correlating the field applied to the quadrupoles with the ion reaching the detector. A mass spectrum can be obtained by scanning the RF field. Only ions of a particular m/z are allowed to pass through.

Electron ionization coupled with quadrupole mass analyzers can be employed in practicing the instant invention. Quadrupole mass analyzers have found new utility in their capacity to interface with electrospray ionization. This interface has three primary advantages. First, quadrupoles are tolerant of relatively poor vacuums (~5×10$^{-5}$ torr), which makes it well-suited to electrospray ionization since the ions are produced under atmospheric pressure conditions. Secondly, quadrupoles are now capable of routinely analyzing up to an m/z of 3000, which is useful because electrospray ionization of proteins and other biomolecules commonly produces a charge distribution below m/z 3000. Finally, the relatively low cost of quadrupole mass spectrometers makes them attractive as electrospray analyzers.

The ion trap mass analyzer was conceived of at the same time as the quadrupole mass analyzer. The physics behind both of these analyzers is very similar. In an ion trap the ions are trapped in a radio frequency quadrupole field. One method of using an ion trap for mass spectrometry is to generate ions externally with ESI or MALDI, using ion optics for sample injection into the trapping volume. The quadrupole ion trap typically consist of a ring electrode and two hyperbolic endcap electrodes. The motion of the ions trapped by the electric field resulting from the application of RF and DC voltages allows ions to be trapped or ejected from the ion trap. In the normal mode the RF is scanned to higher voltages, the trapped ions with the lowest m/z and are ejected through small holes in the endcap to a detector (a mass spectrum is obtained by resonantly exciting the ions and thereby ejecting from the trap and detecting them). As the RF is scanned further, higher m/z ratios become are ejected and detected. It is also possible to isolate one ion species by ejecting all others from the trap. The isolated ions can subsequently be fragmented by collisional activation and the fragments detected. The primary advantages of quadrupole ion traps is that multiple collision-induced dissociation experiments can be performed without having multiple analyzers. Other important advantages include its compact size, and the ability to trap and accumulate ions to increase the signal-to-noise ratio of a measurement.

Quadrupole ion traps can be used in conjunction with electrospray ionization MS/MS experiments in the instant invention.

The earliest mass analyzers separated ions with a magnetic field. In magnetic analysis, the ions are accelerated (using an electric field) and are passed into a magnetic field. A charged particle traveling at high speed passing through a magnetic field will experience a force, and travel in a circular motion with a radius depending upon the m/z and speed of the ion. A magnetic analyzer separates ions according to their radii of curvature, and therefore only ions of a given m/z will be able to reach a point detector at any given magnetic field. A primary limitation of typical magnetic analyzers is their relatively low resolution.

In order to improve resolution, single-sector magnetic instruments have been replaced with double-sector instruments by combining the magnetic mass analyzer with an electrostatic analyzer. The electric sector acts as a kinetic energy filter allowing only ions of a particular kinetic energy to pass through its field, irrespective of their mass-to-charge ratio. Given a radius of curvature, R, and a field, E, applied between two curved plates, the equation R=2V/E allows one to determine that only ions of energy V will be allowed to pass. Thus, the addition of an electric sector allows only ions of uniform kinetic energy to reach the detector, thereby increasing the resolution of the two sector instrument to 100,000. Magnetic double-focusing instrumentation is commonly used with FAB and EI ionization, however they are not widely used for electrospray and MALDI ionization sources primarily because of the much higher cost of these instruments. But in theory, they can be employed to practice the instant invention.

ESI and MALDI-MS commonly use quadrupole and time-of-flight mass analyzers, respectively. The limited resolution offered by time-of-flight mass analyzers, combined with adduct formation observed with MALDI-MS, results in accuracy on the order of 0.1% to a high of 0.01%, while ESI typically has an accuracy on the order of 0.01%. Both ESI and MALDI are now being coupled to higher resolution mass analyzers such as the ultrahigh resolution (>10$^5$) mass analyzer. The result of increasing the resolving power of ESI and MALDI mass spectrometers is an increase in accuracy for biopolymer analysis.

Fourier-transform ion cyclotron resonance (FTMS) offers two distinct advantages, high resolution and the ability to tandem mass spectrometry experiments. FTMS is based on the principle of a charged particle orbiting in the presence of a magnetic field. While the ions are orbiting, a radio frequency (RF) signal is used to excite them and as a result of this RF excitation, the ions produce a detectable image current. The time-dependent image current can then be Fourier transformed to obtain the component frequencies of the different ions which correspond to their m/z.

Coupled to ESI and MALDI, FTMS offers high accuracy with errors as low as ±0.001%. The ability to distinguish individual isotopes of a protein of mass 29,000 is demonstrated.

A time-of-flight (TOF) analyzer is one of the simplest mass analyzing devices and is commonly used with MALDI ionization. Time-of-flight analysis is based on accelerating a set of ions to a detector with the same amount of energy. Because the ions have the same energy, yet a different mass, the ions reach the detector at different times. The smaller ions reach the detector first because of their greater velocity and the larger ions take longer, thus the analyzer is called time-of-flight because the mass is determine from the ions' time of arrival.

The arrival time of an ion at the detector is dependent upon the mass, charge, and kinetic energy of the ion. Since kinetic energy (KE) is equal to ½ mv$^2$ or velocity v=(2 KE/m)$^{1/2}$, ions will travel a given distance, d, within a time, t, where t is dependent upon their m/z.

The magnetic double-focusing mass analyzer has two distinct parts, a magnetic sector and an electrostatic sector. The magnet serves to separate ions according to their mass-to-charge ratio since a moving charge passing through a magnetic field will experience a force, and travel in a circular motion with a radius of curvature depending upon the m/z of the ion. A magnetic analyzer separates ions according to their radii of curvature, and therefore only ions of a given m/z will be able to reach a point detector at any given magnetic field. A primary limitation of typical magnetic analyzers is their relatively low resolution. The electric sector acts as a kinetic energy filter allowing only ions of a particular kinetic energy to pass through its field, irrespective of their mass-to-charge ratio. Given a radius of curvature, R, and a field, E, applied between two curved plates, the equation R=2V/E allows one to determine that only ions of energy V will be allowed to pass. Thus, the addition of an electric sector allows only ions of uniform kinetic energy to reach the detector, thereby increasing the resolution of the two sector instrument.

The new ionization techniques are relatively gentle and do not produce a significant amount of fragment ions, this is in contrast to electron ionization (EI) which produces many fragment ions. To generate more information on the molecular ions generated in the ESI and MALDI ionization sources, it has been necessary to apply techniques such as tandem mass spectrometry (MS/MS), to induce fragmentation. Tandem mass spectrometry (abbreviated MSn—where n refers to the number of generations of fragment ions being analyzed) allows one to induce fragmentation and mass analyze the fragment ions. This is accomplished by collisionally generating fragments from a particular ion and then mass analyzing the fragment ions.

Fragmentation can be achieved by inducing ion/molecule collisions by a process known as collision-induced dissociation (CID) or also known as collision-activated dissociation (CAD). CID is accomplished by selecting an ion of interest with a mass filter/analyzer and introducing that ion into a collision cell. A collision gas (typically Ar, although other noble gases can also be used) is introduced into the collision cell, where the selected ion collides with the argon atoms, resulting in fragmentation. The fragments can then be analyzed to obtain a fragment ion spectrum. The abbreviation MSn is applied to processes which analyze beyond the initial fragment ions (MS2) to second (MS3) and third generation fragment ions (MS4). Tandem mass analysis is primarily used to obtain structural information, such as protein or polypeptide sequence, in the instant invention.

In certain instruments, such as those by JEOL USA, Inc. (Peabody, Mass.), the magnetic and electric sectors in any JEOL magnetic sector mass spectrometer can be scanned together in "linked scans" that provide powerful MS/MS capabilities without requiring additional mass analyzers. Linked scans can be used to obtain product-ion mass spectra, precursor-ion mass spectra, and constant neutral-loss mass spectra. These can provide structural information and selectivity even in the presence of chemical interferences. Constant neutral loss spectrum essentially "lifts out" only the interested peaks away from all the background peaks, hence removing the need for class separation and purification. Neutral loss spectrum can be routinely generated by a number of commercial mass spectrometer instruments (such as the one used in the Example section). JEOL mass spectrometers can also perform fast linked scans for GC/MS/MS and LC/MS/MS experiments.

Once the ion passes through the mass analyzer it is then detected by the ion detector, the final element of the mass spectrometer. The detector allows a mass spectrometer to generate a signal (current) from incident ions, by generating secondary electrons, which are further amplified. Alternatively some detectors operate by inducing a current generated by a moving charge. Among the detectors described, the electron multiplier and scintillation counter are probably the most commonly used and convert the kinetic energy of incident ions into a cascade of secondary electrons. Ion detection can typically employ Faraday Cup, Electron Multiplier, Photomultiplier Conversion Dynode (Scintillation Counting or Daly Detector), High-Energy Dynode Detector (HED), Array Detector, or Charge (or Inductive) Detector.

The introduction of computers for MS work entirely altered the manner in which mass spectrometry was performed. Once computers were interfaced with mass spectrometers it was possible to rapidly perform and save analyses. The introduction of faster processors and larger storage capacities has helped launch a new era in mass spectrometry. Automation is now possible allowing for thousands of samples to be analyzed in a single day. Te use of computer also helps to develop mass spectra databases which can be used to store experimental results. Software packages not only helped to make the mass spectrometer more user friendly but also greatly expanded the instrument's capabilities.

The ability to analyze complex mixtures has made MALDI and ESI very useful for the examination of proteolytic digests, an application otherwise known as protein mass mapping. Through the application of sequence specific proteases, protein mass mapping allows for the identification of protein primary structure. Performing mass analysis on the resulting proteolytic fragments thus yields information on fragment masses with accuracy approaching ±5 ppm, or ±0.005 Da for a 1,000 Da peptide. The protease fragmentation pattern is then compared with the patterns predicted for all proteins within a database and matches are statistically evaluated. Since the occurrence of Arg and Lys residues in proteins is statistically high, trypsin cleavage (specific for Arg and Lys) generally produces a large number of fragments which in turn offer a reasonable probability for unambiguously identifying the target protein.

The characterization of methylation status of a given polypeptide is extremely important for the study of PRMT and their functions in regulating a number of important biological cellular functions. Sometimes, the exact identity of a polypeptide being analyzed is not certain. In these situations, mass spectrometry has the added advantage of identifying polypeptide sequences containing the methylated arginine residue(s). The primary tools in these protein identification experiments are mass spectrometry, proteases, and computer-facilitated data analysis. As a result of generating intact ions, the molecular weight information on the peptides/proteins are quite unambiguous. Sequence specific enzymes can then provide protein fragments that can be associated with proteins within a database by correlating observed and predicted fragment masses. The success of this strategy, however, relies on the existence of the protein sequence within the database. With the availability of the human genome sequence (which indirectly contain the sequence information of all the proteins in the human body) and genome sequences of other organisms (mouse, rat, Drosophila, *C. elegans*, bacteria, yeasts, etc.), identification of the proteins can be quickly determined simply by measuring the mass of proteolytic fragments.

Protease Digestion

One aspect of the instant invention is that peptide fragments ending with lysine or arginine residues can be used for sequencing with tandem mass spectrometry. While trypsin is the preferred the protease, many different enzymes can be used to perform the digestion to generate peptide fragments ending with Lys or Arg residues. For instance, in page 886 of a 1979 publication of *Enzymes* (Dixon, M. et al. ed., 3rd edition, Academic Press, New York and San Francisco, the content of which is incorporated herein by reference), a host of enzymes are listed which all have preferential cleavage sites of either Arg- or Lys- or both, including Trypsin [EC 3.4.21.4], Thrombin [EC 3.4.21.5], Plasmin [EC 3.4.21.7], Kallikrein [EC 3.4.21.8], Acrosin [EC 3.4.21.10], and Coagulation factor Xa [EC 3.4.21.6]. Particularly, Acrosin is the Trypsin-like enzyme of spermatoza, and it is not inhibited by α1-antitrypsin. Plasmin is cited to have higher selectivity than Trypsin, while Thrombin is said to be even more selective. However, this list of enzymes are for illustration purpose only and is not intended to be limiting in any way. Other enzymes known to reliably and predictably perform digestions to generate the polypeptide fragments as described in the instant invention are also within the scope of the invention.

Sequence and Literature Databases and Database Search

The raw data of mass spectrometry will be compared to public, private or commercial databases to determine the identity of polypeptides.

BLAST search can be performed at the NCBI's (National Center for Biotechnology Information) BLAST website.

According to the NCBI BLAST website, BLAST® (Basic Local Alignment Search Tool) is a set of similarity search programs designed to explore all of the available sequence databases regardless of whether the query is protein or DNA. The BLAST programs have been designed for speed, with a minimal sacrifice of sensitivity to distant sequence relationships. The scores assigned in a BLAST search have a well-defined statistical interpretation, making real matches easier to distinguish from random background hits. BLAST uses a heuristic algorithm which seeks local as opposed to global alignments and is therefore able to detect relationships among sequences which share only isolated regions of similarity (Altschul et al., 1990, J. Mol. Biol. 215: 403–10). The BLAST website also offer a "BLAST course," which explains the basics of the BLAST algorithm, for a better understanding of BLAST.

For protein sequence search, several protein-protein BLAST can be used. Protein BLAST allows one to input protein sequences and compare these against other protein sequences. "Standard protein-protein BLAST" takes protein sequences in FASTA format, GenBank Accession numbers or GI numbers and compares them against the NCBI protein databases (see below).

"PSI-BLAST" (Position Specific Iterated BLAST) uses an iterative search in which sequences found in one round of searching are used to build a score model for the next round of searching. Highly conserved positions receive high scores and weakly conserved positions receive scores near zero. The profile is used to perform a second (etc.) BLAST search and the results of each "iteration" used to refine the profile. This iterative searching strategy results in increased sensitivity.

"PHI-BLAST" (Pattern Hit Initiated BLAST) combines matching of regular expression pattern with a Position Specific iterative protein search. PHI-BLAST can locate other protein sequences which both contain the regular expression pattern and are homologous to a query protein sequence.

"Search for short, nearly exact sequences" is an option similar to the standard protein-protein BLAST with the parameters set automatically to optimize for searching with short sequences. A short query is more likely to occur by chance in the database. Therefore increasing the Expect value threshold, and also lowering the word size is often necessary before results can be returned. Low Complexity filtering has also been removed since this filters out larger percentage of a short sequence, resulting in little or no query sequence remaining. Also for short protein sequence searches the Matrix is changed to PAM-30 which is better suited to finding short regions of high similarity.

The databases that can be searched by the BLAST program is user selected, and is subject to frequent updates at NCBI. The most commonly used ones are:

Nr: All non-redundant GenBank CDS translations+PDB+SwissProt+PIR+PRF;

Month: All new or revised GenBank CDS translation+PDB+SwissProt+PIR+PRF released in the last 30 days;

Swissprot: Last major release of the SWISS-PROT protein sequence database (no updates);

Drosophila genome: Drosophila genome proteins provided by Celera and Berkeley Drosophila Genome Project (BDGP);

S. cerevisiae: Yeast (Saccharomyces cerevisiae) genomic CDS translations;

Ecoli: Escherichia coli genomic CDS translations;

Pdb: Sequences derived from the 3-dimensional structure from Brookhaven Protein Data Bank;

Alu: Translations of select Alu repeats from REPBASE, suitable for masking Alu repeats from query sequences. It is available by anonymous FTP from the NCBI website. See "Alu alert" by Claverie and Makalowski, Nature vol. 371, page 752 (1994).

Some of the BLAST databases, like SwissProt, PDB and Kabat are complied outside of NCBI. Other like ecoli, dbEST and month, are subsets of the NCBI databases. Other "virtual Databases" can be created using the "Limit by Entrez Query" option.

The Welcome Trust Sanger Institute offer the Ensembl sofeware system which produces and maintains automatic annotation on eukaryotic genomes. All data and codes can be downloaded without constraints from the Sanger Centre website. The Centre also provides the Ensembl's International Protein Index databases which contain more than 90% of all known human protein sequences and additional prediction of about 10,000 proteins with supporting evidence. All these can be used for database search purposes.

In addition, many commercial databases are also available for search purposes. For example, Celera has sequenced the whole human genome and offers commercial access to its proprietary annotated sequence database (Discovery™ database).

Various softwares can be employed to search these databases. The probability search sofeware Mascot (Matrix Science Ltd.). Mascot utilizes the Mowse search algorithm and scores the hits using a probabilistic measure (Perkins et al., 1999, Electrophoresis 20: 3551–3567, the entire contents are incorporated herein by reference). The Mascot score is a function of the database utilized, and the score can be used to assess the null hypothesis that a particular match occurred by chance. Specifically, a Mascot score of>46 implies that the chance of a random hit is less than 5%. However, the total score consists of the individual peptide scores, and occasionally, a high total score can derive from many poor hits. To exclude this possibility, only "high quality" hits— those with a total score >46 with at least a single peptide match with a score of 30 ranking number 1-are considered.

Other similar softwares can also be used according to manufacturer's suggestion.

To determine if a particular protein is novel, that is, whether it is not previously found to localize to a particular subcellular compartment or organelle, further search of bioinformatics databases are necessary. One useful database for this type of literature search is PubMed.

PubMed, available via the NCBI Entrez retrieval system, was developed by the National Center for Biotechnology Information (NCBI) at the National Library of Medicine (NLM), located at the National Institutes of Health (NIH). The PubMed database was developed in conjunction with publishers of biomedical literature as a search tool for accessing literature citations and linking to full-text journal articles at web sites of participating publishers.

Publishers participating in PubMed electronically supply NLM with their citations prior to or at the time of publication. If the publisher has a web site that offers full-text of its journals, PubMed provides links to that site, as well as sites to other biological data, sequence centers, etc. User registration, a subscription fee, or some other type of fee may be required to access the full-text of articles in some journals.

In addition, PubMed provides a Batch Citation Matcher, which allows publishers (or other outside users) to match their citations to PubMed entries, using bibliographic information such as journal, volume, issue, page number, and year. This permits publishers easily to link from references in their published articles directly to entries in PubMed.

PubMed provides access to bibliographic information which includes MEDLINE as well as:

The out-of-scope citations (e.g., articles on plate tectonics or astrophysics) from certain MEDLINE journals, primarily general science and chemistry journals, for which the life sciences articles are indexed for MEDLINE.

Citations that precede the date that a journal was selected for MEDLINE indexing.

Some additional life science journals that submit full text to PubMed Central and receive a qualitative review by NLM.

PubMed also provides access and links to the integrated molecular biology databases included in NCBI's Entrez retrieval system. These databases contain DNA and protein sequences, 3-D protein structure data, population study data sets, and assemblies of complete genomes in an integrated system.

MEDLINE is the NLM's premier bibliographic database covering the fields of medicine, nursing, dentistry, veterinary medicine, the health care system, and the preclinical sciences. MEDLINE contains bibliographic citations and author abstracts from more than 4,300 biomedical journals published in the United States and 70 other countries. The file contains over 11 million citations dating back to the mid-1960's. Coverage is worldwide, but most records are from English-language sources or have English abstracts.

PubMed's in-process records provide basic citation information and abstracts before the citations are indexed with NLM's MeSH Terms and added to MEDLINE. New in process records are added to PubMed daily and display with the tag [PubMed—in process]. After MeSH terms, publication types, GenBank accession numbers, and other indexing data are added, the completed MEDLINE citations are added weekly to PubMed.

Citations received electronically from publishers appear in PubMed with the tag [PubMed—as supplied by publisher]. These citations are added to PubMed Tuesday through Saturday. Most of these progress to In Process, and later to MEDLINE status. Not all citations will be indexed for MEDLINE and are tagged, [PubMed—as supplied by publisher].

The Batch Citation Matcher allows users to match their own list of citations to PubMed entries, using bibliographic information such as journal, volume, issue, page number, and year. The Citation Matcher reports the corresponding PMID. This number can then be used to easily to link to PubMed. This service is frequently used by publishers or other database providers who wish to link from bibliographic references on their web sites directly to entries in PubMed.

While the invention has been disclosed in connection with separating individual or multiple liquid samples into constituent parts through the use of nanoflow liquid chromatography, various modifications and improvements thereon will become readily apparent to those skilled in the art, such as chromatographic processes that include affinity chromatography, hydrophobic chromatography such as reverse phase, ion-exchange chromatography, gel filtration, hydroxylapatite chromatography, and size exclusion chromatography.

Exemplification

The invention now being generally described, it will be more readily understood by reference to the following examples which are included merely for purposes of illustration of certain aspects and embodiments of the present invention, and are not intended to limit the scope of the invention.

EXAMPLE 1

Synthetic Peptides

To determine if mass spectrometry could be used to distinguish between peptides that have symmetrically versus asymmetrically dimethylated arginines, synthetic peptides with each type of modification were created using standard FMOC chemistry (Meadows et al. 1997 *Immunity* 6:273–281, incorporated herein by reference). The synthesized peptides were modeled on peptides known to be arginine-dimethylated in vivo. Three versions of each were made: unmodified and with asymmetrically and with symmetrically dimethylated arginines. The sequences made were as follows, where R* indicates the site of modification:

VAGR*GR*GR*GGPRR (SEQ ID NO: 1)

VAGRGR*GRGGPRR (SEQ ID NO: 2)

VAAR*GR*GR*GMGR*GK (SEQ ID NO: 3)

VAARGRGR*GMGRGK (SEQ ID NO: 4)

VGGR*GR*GR*GTAAPR (SEQ ID NO: 5)

LGGR*GR*GR (SEQ ID NO: 6)

NSSR*SR*FYSGF (SEQ ID NO: 7)

GR*GLSLSR (SEQ ID NO: 8)

RPIGGR*GGYYGA (SEQ ID NO: 9)

Figure 2:
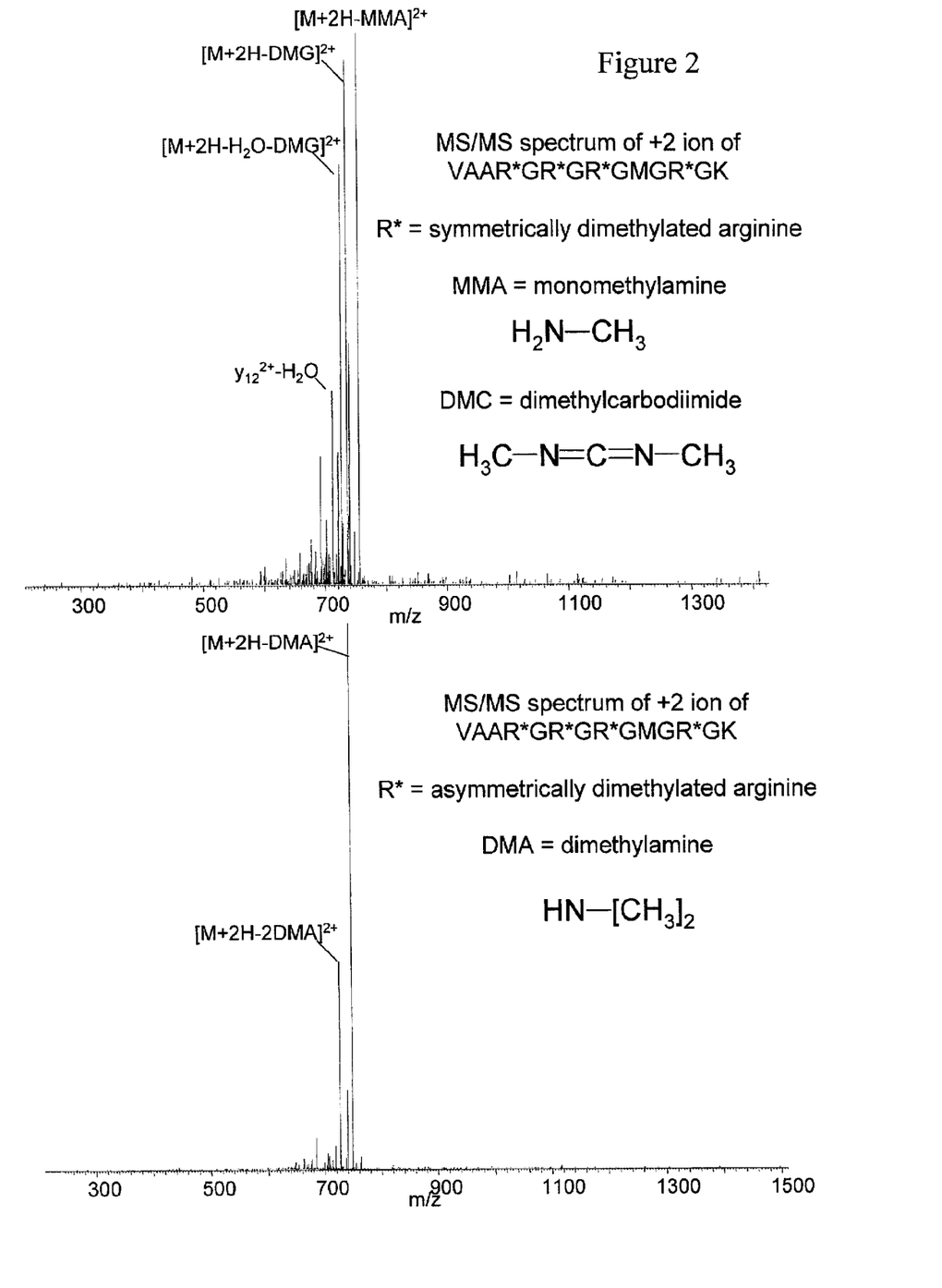
FIG. 2 illustrates that peptides display very strong ions in their MS/MS spectra due to fragmentation of the modified arginine; specifically, the symmetrically dimethylated peptides show strong neutral loss of monomethylamine (MMA) and of dimethylcarbodiimide (DMC) while the asymmetrically dimethylated peptides display a neutral loss of dimethylamine (DMA). The peptide sequence VAAR*GR*GR*GMGR*GK in this figure is represented by SEQ ID NO: 3.

The synthesized peptides were diluted to approximately 1 pmol/μl and infused at approximately 200 nl/min into a Finnigan LCQ ion trap mass spectrometer. MS/MS spectra were obtained from the doubly (+2) and triply (+3) protonated peptides. The spectra for each "pair" of synthetic peptides (i.e., the symmetrically and asymmetrically modified version) were compared. In each case the spectra showed significant differences. Notably, these peptides display very strong ions in their MS/MS spectra due to fragmentation of the modified arginine; specifically, the symmetrically dimethylated peptides show strong neutral loss of monomethylamine (MMA) and of dimethylcarbodiimide (DMC) while the asymmetrically dimethylated peptides display a neutral loss of dimethylamine (DMA) (see FIG. 2). This loss is observed most dramatically from the +2 parent ion but also occurs from selected b- and y-type ions within the spectra. FIG. 2 shows the spectra for one of these synthetic peptides, VAAR*GR*GR*GMGR*GK (SEQ ID NO: 3). The spectrum for both the symmetrically and the asymmetrically dimethylated version of this peptide is dominated by the appropriate neutral loss(es); the neutral loss from the modified arginines is apparently a very facile fragmentation, analogous to the neutral loss of phosphoric acid from phosphopeptides (DeGnore et al. 1998 *J. Am. Soc. Mass Spectrom.* 9: 1175–1188). Table 1 shows the relative abundance of these diagnostic neutral losses from all the peptides synthesized.

TABLE 1

| Symmetrically dimethylated peptides | | |
|---|---|---|
| Sequence | % abundance of $[M + 2H - MMA]^{2+}$ | % abundance of $[M + 2H - DMC]^{2+}$ |
| (SEQ ID NO:2) VAGRGR*GRGGPRR | 100 | 95 |
| (SEQ ID NO:1) VAGR*GR*GR*GGPRR | 100 | 80 |
| (SEQ ID NO:3) VAAR*GR*GR*GMGR*GK | 95 | 95 |
| (SEQ ID NO:4) | 75 | 100 |

TABLE 1-continued

| VAARGRGR*GMGRGK | | |
|---|---|---|
| (SEQ ID NO:9)<br>RPIGGR*GGYYGA | 12 | 20 |
| (SEQ ID NO:5)<br>VGGR*GR*GR*GTAAPR | 50 | 100 |
| (SEQ ID NO:7)<br>NSSR*SR*FYSGF | 100 | 65 |
| (SEQ ID NO:6)<br>LGGR*GR*GR | 95 | 60 |
| (SEQ ID NO:8)<br>GR*GLSLSR | 65 | 10 |

| Asymmetrically dimethylated peptides | |
|---|---|
| Sequence | % abundance of<br>$[M + 2H - DMA]^{2+}$ |
| (SEQ ID NO:2)<br>VAGRGR*GRGGPRR | 100 |
| (SEQ ID NO:1)<br>VAGR*GR*GR*GGPRR | 100 |
| (SEQ ID NO:3)<br>VAAR*GR*GR*GMGR*GK | 100 |
| (SEQ ID NO:4)<br>VAARGRGR*GMGRGK | 100 |
| (SEQ ID NO:9)<br>RPIGGR*GGYYGA | 20 |
| (SEQ ID NO:7)<br>NSSR*SR*FYSGF | 12 |
| (SEQ ID NO:6)<br>LGGR*GR*GR | 65 |
| (SEQ ID NO:8)<br>GR*GLSLSR | 15 |

EXAMPLE 2
Myelin Basic Protein

In a further experiment peptides resulting from the tryptic digest of myelin basic protein were analyzed using the method disclosed herein.

Myelin basic protein (Sigma, St. Louis, Mo.) was digested with trypsin (50:1 w/w) overnight at 37° C. One pmole digest was loaded to a 360×100 μm C18 precolumn and washed extensively with 0.1% acetic acid. The precolumn was then butt-connected to a 360×50 μm C18 analytical column with a pulled emitter tip (~2 μm) (1). Peptides were gradient eluted (0–36% acetonitrile in 0.1% acetic acid in 100 minutes) for nHPLC/μESI/MS(/MS) analysis using an LCQ DecaXP ion trap mass spectrometer. The mass spectrometer was operated in standard data-dependent mode, subjecting the five most abundant ions observed during MS to MS/MS in subsequent scans.

Figure 3:
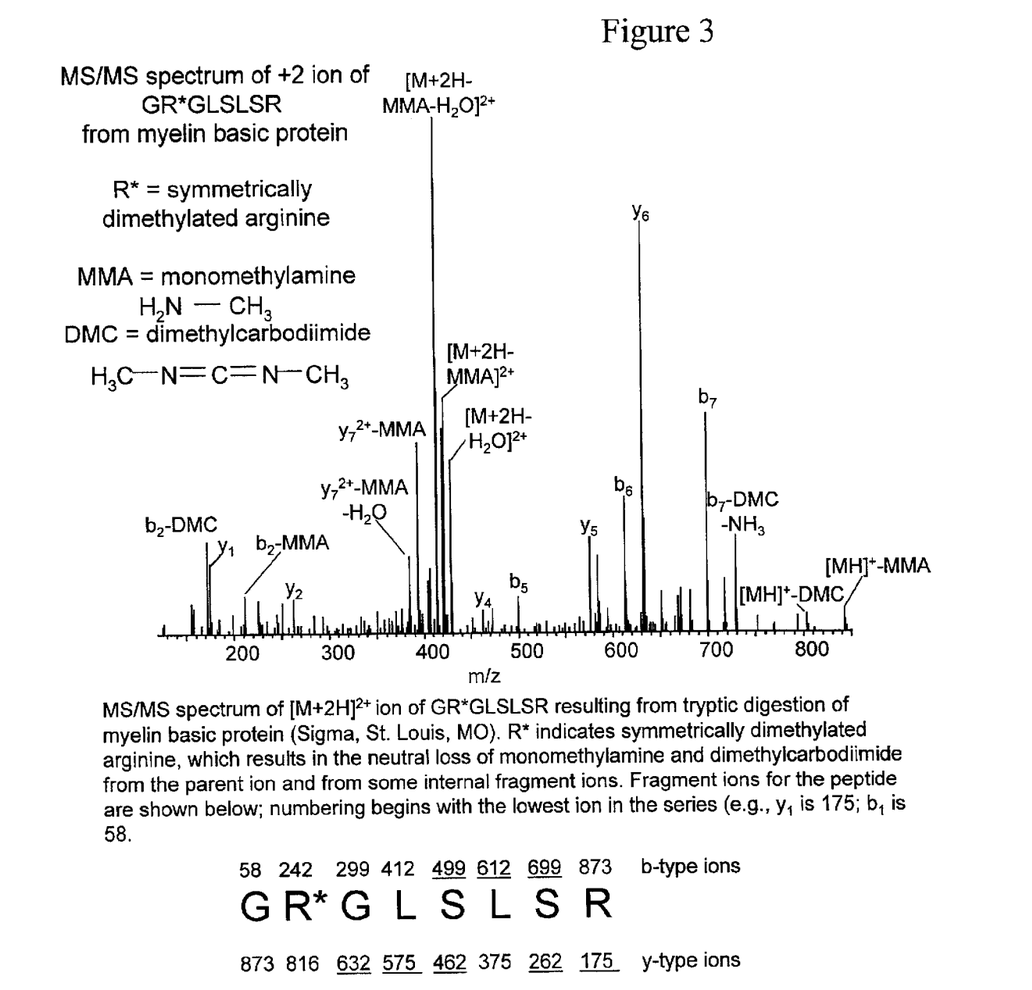
FIG. 3 shows the MS/MS spectrum of peptide GR*GLSLSR (SEQ ID NO: 8) resulting from tryptic digestion of myelin basic protein. R* indicates a symmetrically dimethylated arginine residue.

Post-acquisition, MS/MS spectra were examined for the neutral losses indicative of dimethylated arginine that are described above. An MS/MS spectrum exhibiting apparent neutral loss of monomethylamine from a peptide of nominal mass 872 was observed (see FIG. 3). SEQUEST database searching identified this peptide as GR*GLSLSR (SEQ ID NO: 8), where R* is dimethylated arginine. Manual examination confirmed this identification and identified several b- and y-type ions exhibiting neutral losses associated with symmetrically dimethylated arginine residues. This site has previously been shown to be symmetrically dimethylated, indicating that this method can successfully identify both sites and the type of arginine methylation in a single, two hour experiment.

EXAMPLE 3
pICln

SmD proteins were shown to interact with the protein pICln. FLAG tagged pICln was immunoprecipitated and the SmD proteins were analyzed to determine if SmD peptides from this complex were symmetrically dimethylated on arginine residues. HEK293 cells expressing FLAG-pICln were lysed as previously described (Figeys D, et al., Mass spectrometry for the study of protein-protein interactions. Methods. Jul. 24, 2001 (3): 230–9) and lysate was applied to a 50 μl (bed volume) column of anti-FLAG M2 agarose (Sigma). The column was washed with 30 column volumes of lysis buffer, followed by 10 column volumes of PBS pH 7.2. Proteins were eluted in 50 mM phosphoric acid pH 1.7 and digested with trypsin. The resulting tryptic peptides were eluted with acid. An aliquot (4%) of the eluate was loaded to a 360×100 μm C18 precolumn and washed extensively with 0.1% acetic acid. The precolumn was then butt-connected to a 360×50 μm C18 analytical column with a pulled emitter tip (~2 μm) (1). Peptides were gradient eluted (0–36% acetonitrile in 0.1% acetic acid in 100 minutes) for nHPLC/μESI/MS(/MS) analysis using an LCQ DecaXP ion trap mass spectrometer. The mass spectrometer was operated in standard data-dependent mode, subjecting the five most abundant ions observed during MS to MS/MS in subsequent scans.

Post-acquisition, MS/MS spectra were examined for the neutral losses indicative of dimethylated arginine that are described above. Multiple MS/MS spectra exhibiting apparent neutral losses of monomethylamine and dimethylcarbodi-imide from a peptide of nominal mass 2241.8 were observed (see FIG. 4). The mass of the peptide corresponds to a C-terminal peptide from SmD3, which is known to associate with a 20S methylosome complex containing pICln and is also known to contain four symmetrically dimethylated arginine residues (2,3). MS/MS spectra from multiple charge states of this peptide (+2, +3, +4, and +5) were observed, all strongly resembling MS/MS spectra from a synthetic peptide made to mimic the SmD3 peptide (see FIG. 1). Thus in a single two hour analysis, this method successfully identified arginine methylation sites from a pICln-associated protein and identified the type of modification (symmetrical vs. asymmetrical), indicating the utility of this approach.

Thus the presence of the $[M+2H-MMA]^{2+}$ and $[M+2H-DMC]^{2+}$ can be used as a diagnostic for peptides containing symmetrically dimethylated arginines, while the presence of the $[M+2H-DMA]^{2+}$ ion can be used as a diagnostic for peptides containing asymmetrically dimethylated arginines.

In summary, the MS/MS spectra of peptides containing dimethylated arginines display ions that indicate the type of dimethylation, symmetrical vs. asymmetrical. The data set generated indicates that the abundance of these ions is such that they can be used to screen for peptides containing dimethyl-arginine. Where the spectra contains enough fragmentation information, the sequence of the peptides can then be determined and thus methyltransferase substrates defined.

REFERENCES

1. Martin S. E., Shabanowitz J., Hunt D. F., and Marto J. A. Anal Chem. 2000 72(18): 4266–74.
2. Friesen W J, Paushkin S, Wyce A, Massenet S, Pesiridis G S, Van Duyne G, Rappsilber J, Mann M, Dreyfuss G. Mol Cell Biol. 2001; 21(24): 8289–300.
3. Friesen W J, Massent S, Wyce A, Dreyfuss G. Mol Cell. 2001; 7(5):1111–7.

All patents, patent applications, and cited references are hereby incorporated by reference.

We claim:

1. A method for identifying the structure of a dimethylarginine comprising:

(i) obtaining, by mass spectroscopy, a neutral loss spectrum of a peptide containing a dimethylarginine, and (ii) ascertaining if the neutral loss spectrum shows one or both of neutral loss of monomethylamine (MMA), dimethylcarbodiimide (DMC), and/or neutral loss of dimethylarginine (DMA), wherein neutral loss of monomethylamine (MIMA) and of dimethylcarbodiimide (DMC) indicates the presence of a symmetrically dimethylated arginine residue, whereas neutral loss of dimethylamine (DMA) indicates the presence of an asymmetrically dimethylated arginine residue.

2. A method for identifying dimethylarginine residues in a peptide, comprising:

(i) identifying the presence of dimethylarginine residues from mass spectra of said peptide obtained under conditions in which the spectra reveal mass modification by methylation, if any, of arginine residues in said peptide;

(ii) ascertaining the nature of the methylation of a dimethylarginine residue identified in step (i) by determining if a neutral loss spectrum of said peptide shows one or both of neutral loss of monomethylamine (MMA), dimethylcarbodiimide (DMC), and/or neutral loss of dimethylamine (DMA), wherein neutral loss of monomethylamine (MMA) and of dimethylcarbodiimide (DMC) indicates the presence of a symmetrically dimethylated arginine residue, whereas neutral loss of dimethylamine (DMA) indicates the presence of a asymmetrically dimethylated arginine residue.

3. A method for identifying substrates of a protein arginine methyltransferase comprising:

(i) obtaining mass spectra for one or more sample polypeptides which have been exposed to a protein arginine methyltransferase (PRMT) under conditions wherein methylation, if any, of arginine residues in said one or more sample polypeptides;

(ii) identifying the presence of dimethylarginine residues in said one or more sample polypeptides by the presence of mass modified arginine in the mass spectra; and (iii) ascertaining the nature of the methylation of a dimethylarginine residue identified in step (i) by determining if a neutral loss spectrum of said one or more sample polytides shows one or both of neutral loss of monomethylamine (MMA), dimethylcarbodiimide (DMC), and/or neutral loss of dimethylamine (DMA), wherein neutral loss of monomethylamine (MMA) and of dimethylcarbodiimide (DMC) indicates the presence of a symmetrically dimethylated arginine residue whereas neutral loss of dimethylamine (DMA) indicates the presence of a asymmetrically dimethylated arginine residue.

4. The method of claim 3, wherein said one or more sample polypeptides constitute a library of sample polypeptides.

5. The method of anyone of claims 2–3 and 4, wherein the neutral loss spectrum is generated from said mass spectra.

6. The method of anyone of claims 1–3 and 4, wherein ionization of said peptide or polypeptides is accomplished by matrix-assisted laser desorption (MALDI) ionization, electrospray (ESI), or electron impact (EI).

7. The method of anyone of claims 1–3 and 4, wherein the spectrum is obtained using ESI-MS/MS.

* * * * *

UNITED STATES PATENT AND TRADEMARK OFFICE
CERTIFICATE OF CORRECTION

PATENT NO. : 6,747,273 B2
DATED : June 8, 2004
INVENTOR(S) : Brame et al.

It is certified that error appears in the above-identified patent and that said Letters Patent is hereby corrected as shown below:

Column 25,
Line 35, "dimethylarginine" should read -- dimethylamine --;
Line 36, "MIMA" should read -- MMA --;

Column 26,
Lines 52, 54 and 58, the word "anyone" should read -- any one --.

Signed and Sealed this

Nineteenth Day of April, 2005

JON W. DUDAS
*Director of the United States Patent and Trademark Office*